US011127483B2

United States Patent
Baran et al.

(10) Patent No.: US 11,127,483 B2
(45) Date of Patent: Sep. 21, 2021

(54) COMPUTATIONAL PIPELINE FOR ANTIBODY MODELING AND DESIGN

(71) Applicant: IGC BIO, INC., Brookline, MA (US)

(72) Inventors: Dror Baran, Tel Aviv (IL); Lior Zimmerman, Tel Aviv (IL)

(73) Assignee: IGC BIO, INC., Cambridge, MA (US)

( * ) Notice: Subject to any disclaimer, the term of this patent is extended or adjusted under 35 U.S.C. 154(b) by 526 days.

(21) Appl. No.: 15/912,059

(22) Filed: Mar. 5, 2018

(65) Prior Publication Data

US 2018/0260518 A1 Sep. 13, 2018

Related U.S. Application Data

(60) Provisional application No. 62/468,069, filed on Mar. 7, 2017.

(51) Int. Cl.
| | |
|---|---|
| *G16B 15/00* | (2019.01) |
| *G16B 30/00* | (2019.01) |
| *G16B 35/10* | (2019.01) |
| *C07K 16/00* | (2006.01) |

(52) U.S. Cl.
CPC .............. *G16B 15/00* (2019.02); *C07K 16/00* (2013.01); *C07K 16/005* (2013.01); *G16B 30/00* (2019.02); *G16B 35/10* (2019.02); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 6,127,524 A | 10/2000 | Casipit et al. | |
| 7,315,786 B2 | 1/2008 | Dahiyat et al. | |
| 2003/0022240 A1 | 1/2003 | Luo et al. | |
| 2003/0054407 A1 | 3/2003 | Luo | |
| 2003/0059827 A1 | 3/2003 | Gonzalez et al. | |
| 2004/0110226 A1 | 6/2004 | Lazar et al. | |
| 2010/0093980 A1 | 4/2010 | Lugovskoy et al. | |
| 2011/0172981 A1* | 7/2011 | Al-Hashimi | G01R 33/465 703/11 |
| 2011/0224100 A1 | 9/2011 | Parmeggiani et al. | |
| 2013/0244940 A1 | 9/2013 | Steiner et al. | |
| 2013/0296221 A1 | 11/2013 | Binz | |
| 2014/0005125 A1 | 1/2014 | Baumann | |
| 2014/0335102 A1 | 11/2014 | Oberlin et al. | |

FOREIGN PATENT DOCUMENTS

| | | |
|---|---|---|
| WO | WO 2016/005969 | 1/2016 |
| WO | WO 2016/086185 | 6/2016 |
| WO | WO 2017/017673 | 2/2017 |
| WO | WO 2017/210148 | 12/2017 |
| WO | WO 2017/210149 | 12/2017 |
| WO | WO 2017/214211 | 12/2017 |

OTHER PUBLICATIONS

Marco et al. ChemMedChem (2007), 2(10), 1388-1401.*
Rongan et al. Perspectives in Drug Discovery and Design, Sep. 10, 2011, 181-209, 1998.*
Barderas et al., "Affinity maturation of antibodies assisted by in silico modeling", PNAS, Jul. 1, 2008, vol. 105, No. 26, pp. 9029-9034.
Kuroda et al., "Computer-aided antibody design", Protein Engineering, Design & Selection, 2012, vol. 25, No. 10, pp. 507-521 (published online Jun. 2, 2012).
Smirnov et al., "Robotic QM/MM-driven maturation of antibody combining sites", Sci. Adv. 2016;2:e1501695, Oct. 19, 2016.
Fleishman, S. et al., "Role of the Biomolecular Energy Gap in Protein Design, Structure, and Evolution", Cell 149, Apr. 13, 2012, pp. 262-273.
Clark, L.A. et al., "Affinity enhancement of an in vivo matured therapeutic antibody using structure-based computational design", Protein Sci., 2006, 15(5), p. 949-60.
Lippow, S.M. et al., "Computational design of antibody affinity improvement beyond in vivo maturation", Nat. Biotechnol., Oct. 2007, 25(10), p. 1171-6.
Clark, L.A. et al., "An antibody loop replacement design feasibility study and a loop-swapped dimer structure", Protein Eng. Des. Sel., 2009, 22(2), p. 93-101.
Farady, C.J. et al., "Improving the species cross-reactivity of an antibody using computational design", Bioorg. Med. Chem. Lett., Jul. 15, 2009 19(14), p. 3744-7.
Miklos, A.E. et al., "Structure-Based Design of Supercharged, Highly Thermoresistant Antibodies", Chem. Biol., Apr. 20, 2012; 19(4), p. 449-55.
Pantazes et al., "OptCDR: a general computational method for the design of antibody complementarity determining regions for targeted epitope binding", Protein Engineering, Design & Selection, vol. 23, No. 11, pp. 849-858, 2010.
Pantazes et al., "MAPs: a database of modular antibody parts for predicting tertiary structures and designing affinity matured antibodies", BMC Bioinformatics 2013, 14:168.
Weitzner, B.D. et al., "Blind prediction performance of RosettaAntibody 3.0: Grafting, relaxation, kinematic loop modeling, and full CDR optimization", Proteins, Aug. 2014; 82(8): 1611-1623 (epub. Feb. 12, 2014).

(Continued)

*Primary Examiner* — Michael L Borin
(74) *Attorney, Agent, or Firm* — Mark S. Cohen; Pearl Cohen; Zedek Latzer Baratz LLP

(57) ABSTRACT

This disclosure presents methods for antibody structure prediction and design. We utilize the growing number of antibody structures and sequences are used with powerful protein modeling methods to design and predict antibody structural models up to sub-angstrom accuracy. The invention also relates to systems and methods for generating an antibody library. Specifically, the invention relates to computer-implemented systems and methods for generating an antibody library for a predetermined epitope. The invention further relates to determining structural models of the interface between an antibody and its antigen. The invention also relates to determining structural models of an unbound complementarity determining region of an antibody.

8 Claims, 9 Drawing Sheets

(56) References Cited

OTHER PUBLICATIONS

Shirai, H. et al., "High-resolution modeling of antibody structures by a combination of bioinformatics, expert knowledge, and molecular simulations", Proteins, published online Apr. 22, 2014 in Wiley Online Library (wileyonlinelibrary.com).

Smadbeck, J. et al., "Protein WISDOM: A Workbench for in silico De novo Design of BioMolecules", J. Vis. Exp., (77), e50476, May 10, 2013, p. 1-25.

Khoury, G.A. et al., "Protein folding and de novo protein design for biotechnological applications", Trends in Biotechnology, Feb. 2014; 32(2), p. 99-109.

Offredi, F. et al., "De novo Backbone and Sequence Design of an Idealized α/β-barrel Protein: Evidence of Stable Tertiary Structure", J. Mol. Biol., 2003, 325(1), p. 163-74.

Figueroa, M. et al., "Octarellin VI: Using Rosetta to Design a Putative Artificial (β/α)$_8$ Protein", PLoS One, 8(8), e71858, Aug. 19, 2013.

Parra R.G., et al., "Protein Frustratometer 2: a tool to localize energetic frustration in protein molecules, now with electrostatics ", Nucleic Acids Res., 2016, 44:W356-360.

Goldenzweig, A. et al., "Automated Structure- and Sequence-Based Design of Proteins for High Bacterial Expression and Stability", Mol Cell., Jul. 21, 2016; 63(2): 337-346.

Campeotto, I. et al., "One-step design of a stable variant of the malaria invasion protein RH5 for use as a vaccine immunogen", Proc. Natl. Acad. Sci., USA, Jan. 31, 2017, 114(5):998-1002.

Rohl, Carol et al., "Protein structure prediction using Rosetta", Methods in Enzymology (2004) 383:66-93.

International Preliminary Report on Patentability, dated Sep. 19, 2019, for corresponding International Application No. PCT/US2018/020964.

Leimgruber et al., "TCRep 3D: An Automated In Silico Approach to Study the Structural Properties of TCR Repertoires", PLoS One, Oct. 28, 2011, vol. 6, No. 10:e26301, pp. 1-15.

International Search Report and Written Opinion of the International Searching Authority, dated Jun. 19, 2018, for corresponding International Application No. PCT/US2018/020964.

King et al., "Removing T-cell epitopes with computational protein design", PNAS 2014, vol. 111, No. 23, pp. 8577-8582.

International Preliminary Report on Patentability, dated Jul. 18, 2019, from corresponding International Application No. PCT/US208/012721.

* cited by examiner

COMPUTATIONAL PIPELINE FOR ANTIBODY MODELING AND DESIGN

CROSS-REFERENCE TO RELATED APPLICATIONS

This application claims priority to U.S. Provisional Patent Application 62/468,069, filed Mar. 7, 2017, which is incorporated by reference herein in its entirety.

FIELD OF THE INVENTION

This disclosure presents methods for antibody structure prediction and design, as well as systems and methods for generating antibody libraries. The growing number of antibody structures and sequences are used with powerful protein modeling methods to design and predict antibody structural models up to sub-angstrom accuracy. Specifically, the invention relates to computer-implemented systems and methods for generating libraries of antibody models for a predetermined epitope. The invention further relates to predicting structure models of the interface between an antibody and its antigen, as well as predicting structure models of complementarity determining regions of an unbound antibody.

BACKGROUND OF THE INVENTION

Monoclonal antibodies (mAbs) have been functioning as therapeutic, diagnostic and research agents since the 1970s. Technology to develop monoclonal antibodies to a specific target was invented in 1975. This technology involves immunizing a certain species to a specific antigen and obtaining the B-lymphocytes from the animal's spleen. The B-lymphocytes are then fused (by chemical- or virus-induced methods) with an immortal myeloma cell line lacking the hypoxanthine-guanine-phosphoribosyltransferase (HGPRT) gene and not containing any other immunoglobulin-producing cells, forming a cell called a hybridoma.

Hybridoma technology has many drawbacks; the production of antibodies is limited by whether or not there is a suitable myeloma cell line available (usually mouse or rat). The stability and/or yield of these antibodies are frequently low and the potential of the resulting molecules to serve as therapeutics is very limited due to host rejection. Moreover, hybridoma technology is biased towards the host proteome thus often hinder successful isolation of antibodies targeting host-target conserved proteins. The newest generation of hybridomas still does not address this problem.

Another highly popular method is to generate monoclonal antibodies using phage display. This involves isolating B-lymphocytes from human blood and then isolating the mRNA and converting it into cDNA using PCR to amplify all the VH and VL segments. An alternate method for antibody library generation is by using synthetic VH and VL segments that is rationally designed and enriched by randomization. These segments are then cloned into a vector (usually as ScFv) next to the PIII protein of a bacteriophage before being used to infect $E.$ $coli$, in order to generate libraries containing more than $10^{10}$ antibody variants by inoculating the library with an additional helper phage. $E.$ $coli$ can then secrete bacteriophage containing the VH and VL segments as part of the bacteriophage coat. Specific VH and VL segments against the antigen are then selected and used to reinoculate $E.$ $coli$ with the bacteriophage. Cells containing the plasmid are then isolated and sequenced. The library is usually generated once, and then, is used against multiple antigens. Since the library is made entirely of human antibodies, the risk of host immune response is lowered significantly.

The methods described above are based mostly on random chance. The ability to generate mAbs to a particular epitope depends mostly on the host immune repertoire. Recent advances in the fields of information technology, computational biology, physics and chemistry—particularly the exponential increase in available antibody crystal structures—have led to the development of rational methods for mAb developments.

Studies in the 1980s, revealed that most of the CDR loops (all but H3) adopt a limited number of conformations called canonical structures. This knowledge has been used in mAb humanization procedures where key residues should be maintained when non-human CDRs are grafted onto human frameworks. The adoption of these canonical CDR structures enabled antibody structure prediction and design with greater accuracy than other de-novo methods. Since CDR-H3 do not adopt canonical structures and are quite diverse—from both structure and sequence perspectives, and since they are very frequently involved in epitope binding, most of the focus of antibody modeling and design was put on them.

In the absence of simple sequence-structure relationships for the remainder of CDR-H3, the conformations can be predicted by exploiting the many methods that have been developed for the more general problem of loop prediction. These methods generally work by first enumerating large numbers of plausible loop conformations, and then predicting which of these is likely to be correct by using conformational energy or a scoring function derived from a database of crystal structures. These methods however come with a heavy price. They are usually computationally intensive and become more difficult as the loops become longer, especially for those longer than ~12 amino acids.

Accordingly, there exists a need for improved systems and methods for generating antibody libraries, as well as for antibody structure prediction and design.

SUMMARY OF THE INVENTION

In one aspect, provided herein are computer implemented methods for generating a library of antibody models targeted to a defined epitope, the method comprising: providing a sequence database of complementarity determining regions (CDRs), as well as a database of backbone dihedral angles for CDR segments compatible with a preselected structural template and based on known antibody 3-D structures; docking said preselected structural template on said epitope; evaluating one or more structural models from said databases using a simulated annealing process; and identifying one or more segment sequences in order to generate a library, thereby generating a library of antibody models to the epitope. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

In another aspect, provided herein are computer implemented methods for generating a 3-D structural model of an antibody-antigen complex, the method comprising: providing a sequence database of complementarity determining regions (CDRs), as well as a database of backbone dihedral angles for CDR segments compatible with a preselected structural template and based on known antibody 3-D structures; providing a predetermined antibody sequence and a predetermined epitope structure for said antigen; docking said preselected structural template on said epitope; evaluating the predetermined antibody structural model having structural conformations of entries from said databases using a simulated annealing process; and optimizing the structural conformation, thereby generating the 3-D structural model of the antibody-antigen complex. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

In a further aspect, provided herein are computer implemented methods for generating a 3-D structural model of an antibody, the method comprising: providing a sequence database of complementarity determining regions (CDRs), as well as a database of backbone dihedral angles for CDR segments compatible with a preselected structural template and based on known antibody 3-D structures; providing a predetermined antibody sequence; evaluating the predetermined antibody sequence having structural conformations of entries from said databases using a simulated annealing process; and optimizing the structural conformation, thereby generating the 3-D structural model of the antibody. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

In an additional aspect, provided herein is a computer readable storage media comprising instructions to perform a method for generating a library of antibody models targeted to a defined epitope, the method comprising: providing a sequence database of complementarity determining regions (CDRs), as well as a database of backbone dihedral angles for CDR segments compatible with a preselected structural template and based on known antibody 3-D structures; docking said preselected structural template on said epitope; evaluating one or more structural models from said databases using a simulated annealing process; and identifying one or more segment sequences in order to generate a library, thereby generating a library of antibody models to the epitope. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

In a yet further aspect, provided herein is a computer readable storage media comprising instructions to perform a method for generating a 3-D structural model of an antibody-antigen complex, the method comprising: providing a sequence database of complementarity determining regions (CDRs), as well as a database of backbone dihedral angles for CDR segments compatible with a preselected structural template and based on known antibody 3-D structures; providing a predetermined antibody sequence and a predetermined epitope structure for said antigen; docking said preselected structural template on said epitope; evaluating the predetermined antibody structural model having structural conformations of entries from said databases using a simulated annealing process; and optimizing the structural conformation, thereby generating the 3-D structural model of the antibody-antigen complex. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

In yet another aspect, provided herein is a computer readable storage media comprising instructions to perform a method for generating a 3-D structural model of an antibody, the method comprising: providing a sequence database of complementarity determining regions (CDRs), as well as a database of backbone dihedral angles for CDR segments compatible with a preselected structural template and based on known antibody 3-D structures; providing a predetermined antibody sequence; evaluating the predetermined antibody sequence having structural conformations of entries from said databases using a simulated annealing process; and optimizing the structural conformation, thereby generating the 3-D structural model of the antibody. In some embodiments, the method further includes generating the databases of CDRs and of backbone dihedral angles for CDR segments, comprising the steps of: selecting an antibody structure to serve as a template; obtaining a set of non-redundant high resolution antibody models; extracting the ScFv portion from each antibody model; cutting each ScFv into segments (e.g., the four segments: VH residues 1-99, an H3 loop; VL residues 1-87; and an L3 loop); generating a Point Specific Scoring Matrix (PSSM) for each segment; and generating database entries for each segment using a macromolecular algorithmic unit.

BRIEF DESCRIPTION OF THE DRAWINGS

The invention will be better understood from a reading of the following detailed description taken in conjunction with the drawings in which like reference designators are used to designate like elements.

DETAILED DESCRIPTION OF THE INVENTION

The invention relates to systems and methods for generating an antibody and/or an antibody library. Specifically, the invention relates to computer-implemented systems and methods for generating an antibody model or library of antibody models targeted to a predetermined epitope. The invention further relates to determining structural models of the interface between a predetermined antibody and its antigen. The invention also relates to determining structural models of a predetermined antibody's unbound complementarity determining region.

Several studies clearly indicate that CDR-H3 can be modeled with good (<2.0 Å) accuracy just by relying on the existing structural database of antibodies. The accuracy of those methods can be greatly improved by incorporating energy-based refinement and knowledge based sampling approaches Gray et al. have developed antibody-modeling software named RosettaAntibody, based on their Rosetta design suite (Rohl, Carol A et al. "Protein structure prediction using Rosetta." *Methods in enzymology* (2004) 383:66-93.). They modeled CDR-H3 loops using fragment taken from the Protein Data Bank (PDB) and relaxed the resulting loops using cyclic coordinate descent. Then, these loops were minimized using the Rosetta minimization procedure.

Figure 9:
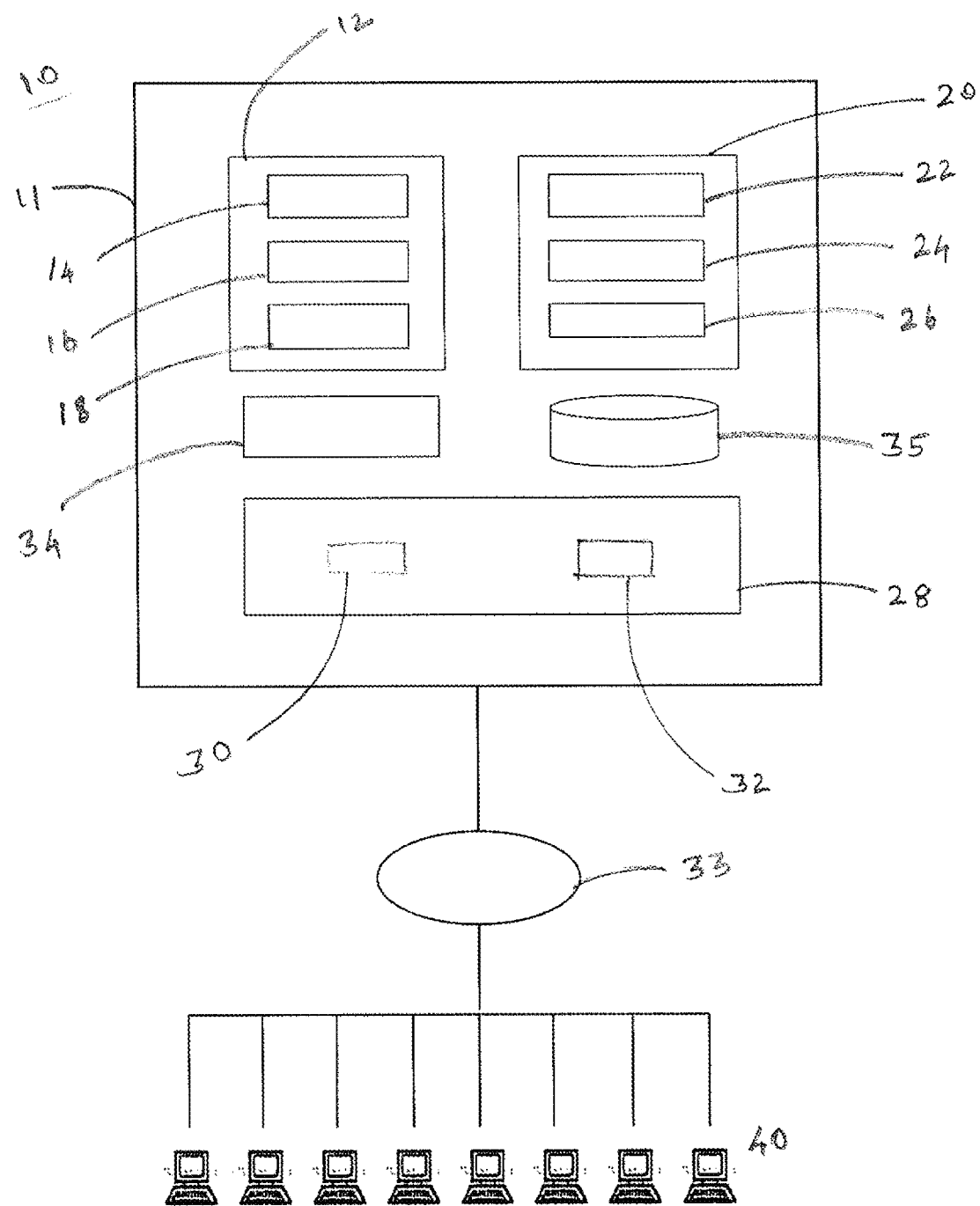
FIG. 9 illustrates a system for generating antibody libraries, according to one embodiment of the invention.

FIG. 9 schematically illustrates one arrangement of a system for generating antibody libraries. Although the FIG. 9 environment shows an exemplary conventional general-purpose digital environment, it will be understood that other computing environments may also be used. For example, one or more embodiments of the invention may use an environment having fewer than or otherwise more than all of the various aspects shown in FIG. 9, and these aspects may appear in various combinations and sub-combinations that will be apparent to one of ordinary skill in the art.

As shown in FIG. 9, a user computer 10 can operate in a networked environment using logical connections to one or more remote computers, such as a remote server 11. The server 11 can be a web server, a router, a network PC, a peer device or other common network node, and typically includes many or all of the elements of a computer. It will be appreciated that the network connections shown in FIG. 9 are exemplary and other techniques for establishing a communications link between the computers can be used. The connection may include a local area network (LAN) and a wide area network (WAN). The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers as well as non-web interfaces can be used to display and manipulate data.

In one aspect, an antibody library can be generated in an online environment. As illustrated in FIG. 9, a user (e.g., researcher) 41 has a user computer 40 with Internet access that is operatively coupled to server 11 via a network 33, which can be an internet or intranet. User computer 40 and server 11 implement various aspects of the invention that is apparent in the detailed description. For example, user computer 40 may be in the form of a personal computer, a tablet personal computer or a personal digital assistant (PDA). Tablet PCs interprets marks made using a stylus in order to manipulate data, enter text, and execute conventional computer application tasks such as spreadsheets, word processing programs, and the like. User computer 40 is configured with an application program that communicates with server 11. This application program can include a conventional browser or browser-like programs.

In one embodiment, server 11 may include a plurality of programmed platforms or units, for example, but are not limited to, a seed generation platform 12, docking platform 20, design platform 28, and an epitope unit 34. Seed generation platform 12 may include one or more programmable units, for example, but are not limited to, a complementarity determining region (CDR) unit 14, a framework unit 16, and an analysis unit 18. Docking platform 20 may include a plurality of programmed platforms or units, for example, but are not limited to, a docking unit 22, an evaluation unit 24, and a selection unit 26. Design platform 28 may include a plurality of programmed platforms or units, for example, but are not limited to, a motif evaluation unit 30 and a library generation unit 32.

The term "platform" or "unit," as used herein, may refer to a collection of programmed computer software codes for performing one or more tasks.

In one embodiment, the systems and methods use a database of antibody complementarity determining regions (CDRs) that are compatible with a preselected template antibody structure. In another embodiment, the database is built through a process of optimizing known CDR sequences for compatibility with template antibody structures using a Point Specific Scoring Matrix (PSSM) and then evaluating an energy score. In a further embodiment, sequence optimization includes sampling a mutation into a position in the sequence under examination, guided by the PSSM distribution and repeating the PSSM based compatibility analysis. In yet another embodiment, a PSSM is generated for every CDR cluster with known 3-D structure prior to sequence optimization.

In one embodiment, the PSSM is created using PSI-BLAST (Position-Specific Iterative Basic Local Alignment Search Tool). In another embodiment, the PSSM is created by counting the number of amino acids, and then calculating the likelihood of each amino acid in each position using a background distribution.

Figure 1:
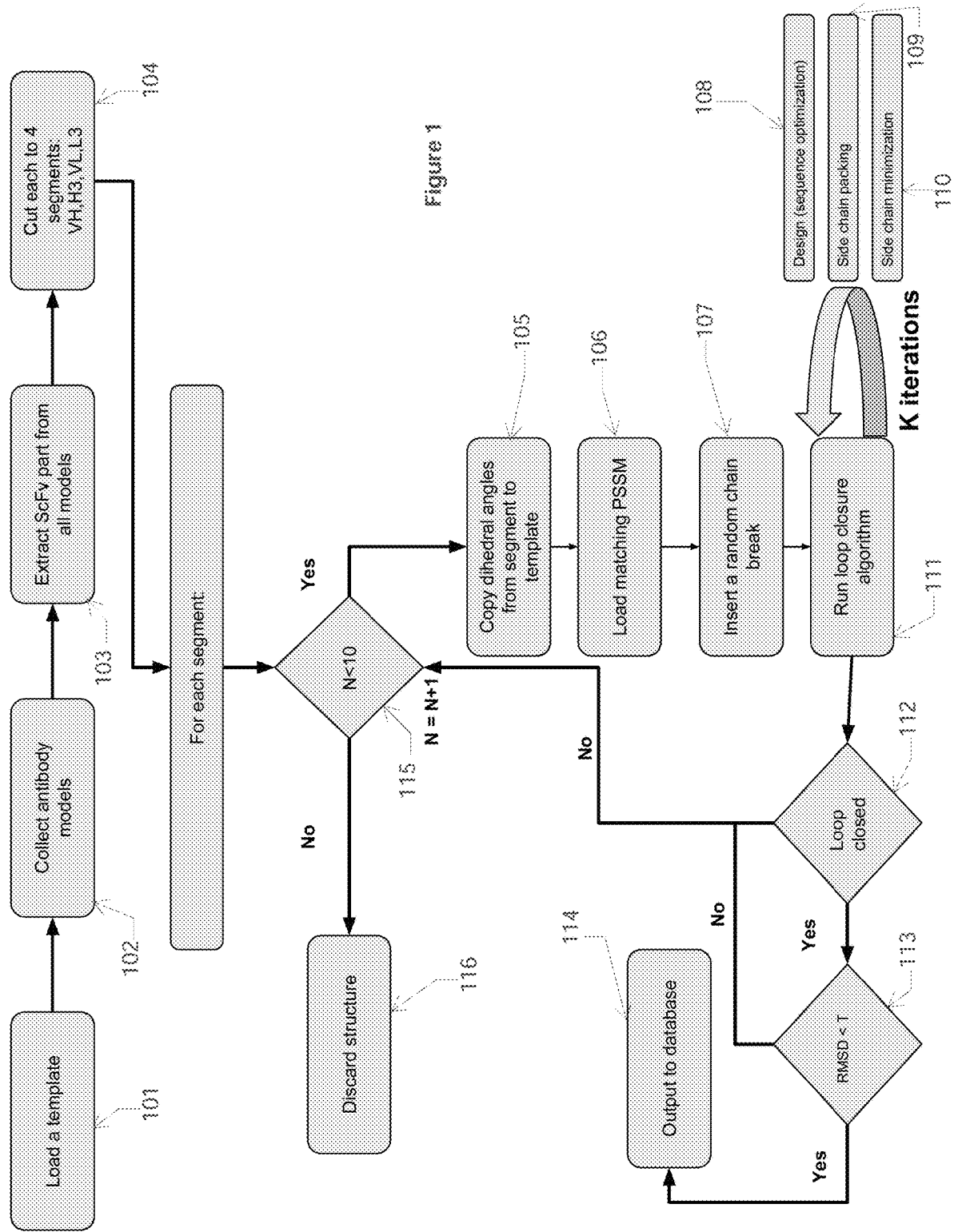
FIG. 1 illustrates a flow chart of a method for generating a segment database, according to one embodiment of the invention.

FIG. 1 schematically illustrates a flow chart of a method for generating a segment database, according to one embodiment of the invention. The process involves PSSM-based sequence optimization (design) approach to compute probabilities for amino acid preferences, according to one embodiment. As shown in item 101, a preselected structural template is uploaded into the analysis input. As shown in item 102, known structural models of the antibodies are collected. As shown in item 103, the ScFv part is extracted from each model, As shown in item 104, each extracted ScFv part is cut each to 4 segments: VH residues 1-99, an H3 loop, VL residues 1-87, and an L3 loop, As shown in item 105, dihedral angles are extracted from a segment. As shown in item 106, the pre-generated PSSM from the segment is loaded into the input. As shown in item 107, random chain breaks are introduced at a random position in the segment under examination. In one embodiment, these chain breaks are introduced in areas that are not part of the secondary structure (α-helix or β-sheet). As shown in item 111, a loop closure algorithm is run using a macro-molecular modeling software suite (e.g., Rosetta) for a preset number of iterations (e.g., K=1000) in order to close the loop. In one embodiment, the loop closure algorithm is CCD. In another embodiment, the loop closure algorithm is Kinematic loop closure. As shown in items 108-110, the loop closure algorithm can include sequence optimization, side-chain packing, and side-chain minimization, said procedures carried out in any order. As shown in item 112, if the loop is not closed after K cycles of the loop closure algorithm, the optimization cycle is repeated. As shown in item 113, if the loop is closed after K cycles of loop closure algorithm, and the Root Mean Square Deviation RMSD of the modeled segment is smaller than a predefined threshold T, then the segment is added to the database (item 114), and if the RMSD of the modeled segment is larger than the predefined threshold T, the optimization cycle is repeated. In one embodiment, the predefined threshold T<1. Å. As shown in item 115, if the loop is not closed after 10 optimization cycles, the structural model is discarded (item 116). As the result, a library of CDR segments compatible with the chosen structural templates is generated.

Figure 2:
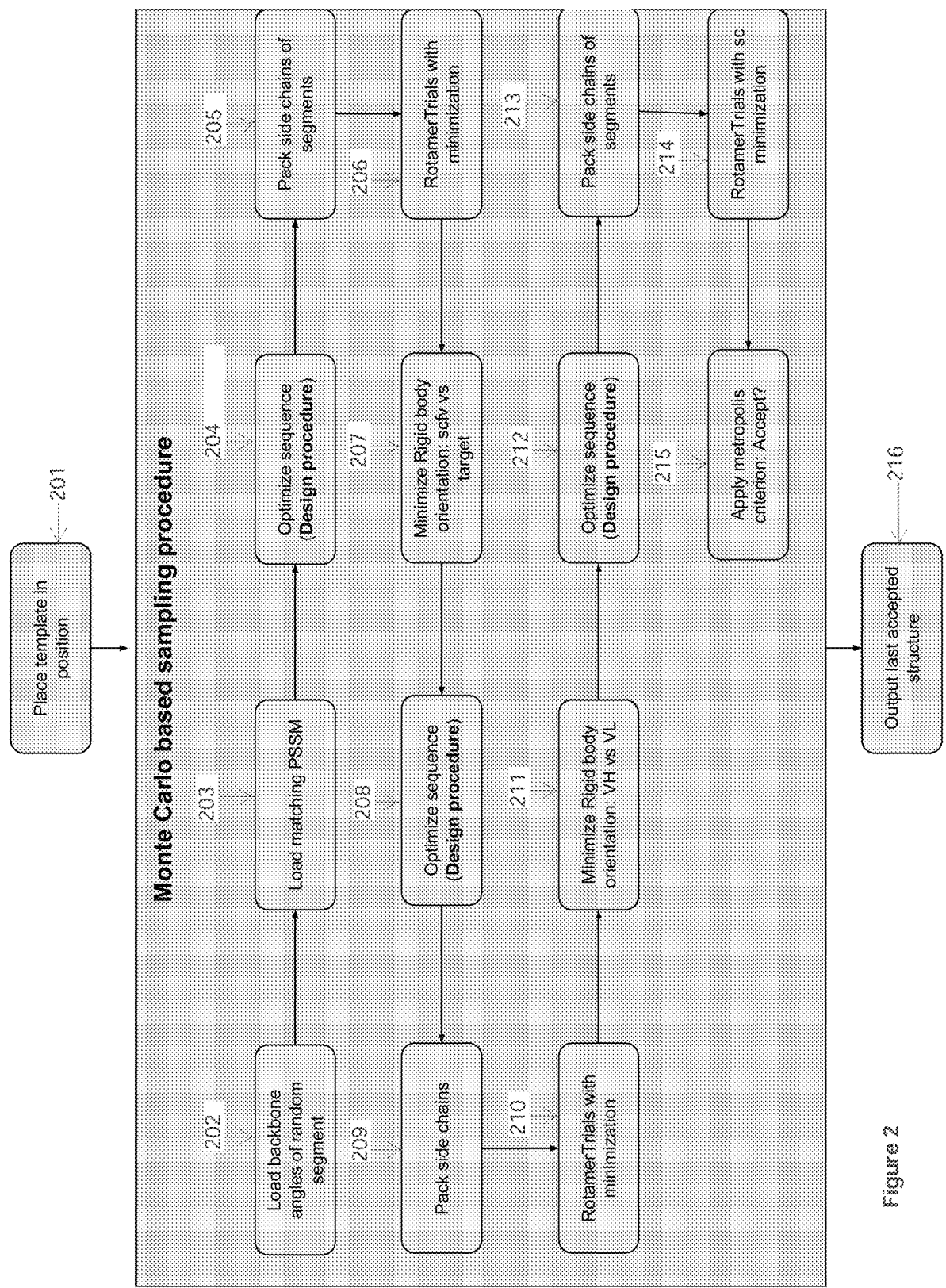
FIG. 2 illustrates a flow chart of a method for designing of an antibody for a target ligand, according to one embodiment of the invention.

FIG. 2 schematically illustrates a flow chart of a method for designing of an antibody for a target ligand, according to one embodiment. The steps can be carried out using any suitable macro-molecular modeling software suite (e.g., Rosetta). As shown in item 201, the structural template is placed in a desired position and orientation relative to a predetermined target epitope. In one embodiment the target epitope is a protein epitope. In a further embodiment, the target epitope is a multiprotein complex. In a yet another embodiment, the target epitope is a small molecule. In yet further embodiment, the target epitope is a carbohydrate. In some embodiments, placement of the template in the desired position is performed by software-mediated docking, or by superimposing the template on an existing antibody-antigen complex, or a combination of multiple methods.

After placing the template, a Monte-Carlo procedure with the metropolis acceptance criteria is carried out for each entry in the segment database for a preset number of iterations (K=250), as shown in items 202-215, in order to simulate annealing. As shown in item 202, the backbone dihedral angles of a segment from the segment database are input into the annealing simulation. As shown in item 203, a PSSM of the segment under examination is input into the annealing simulation. As shown in item 204, a sequence optimization algorithm is run for amino acids that pass a predefined likelihood threshold, as determined using the PSSM. As shown in item 205, the side chains are packed in the selected segment. As shown in item 206, Rotamer-Trials with Minimization is performed. In one embodiment, the RotamerTrials are performed until the score of the complex shows an insignificant change between iterations. In another embodiment, the RotamerTrials are performed for a predetermined number of iterations. In one embodiment, the rotamer trials are performed for at least 5 iterations, at least 6 iterations, at least 7 iterations, at least 8 iterations, at least 9 iterations, at least 10 iterations, or for more than 10 iterations. As shown in item 207, rigid body minimization of the ScFv versus the target is performed. As shown in item 208, a second sequence optimization is performed in a way similar to item 204. As shown in item 209, the side chains are packed in the selected segment in a way similar to item 205. As shown in item 210, cyclical Rotamer-Trials Minimization is performed in a way similar to item 206. As shown in item 211, a rigid body minimization of the VH versus the VL is performed. As shown in item 212, a third sequence optimization is performed in a way similar to item 204. As shown in item 213, the side chains are packed in the selected segment in a way similar to item 205. As shown in item 214, Rotamer-Trials Minimization are performed in a way similar to item 206. As shown in item 215, the structural models that pass predefined metropolis acceptance criterion are accepted for output (item 216). Additional rounds of optimization prior to output (between items 214 and 215 in FIG. 2) are contemplated and generally comprise steps of sequence optimization, side chain packing, rotamer trials and an additional step, wherein said additional step is optimizing the backbone of antibody, optimizing the light and heavy chain orientation, or optimizing the antibody as monomer. As a result, a CDR for an antibody targeting an epitope of choice is generated.

Figure 3:
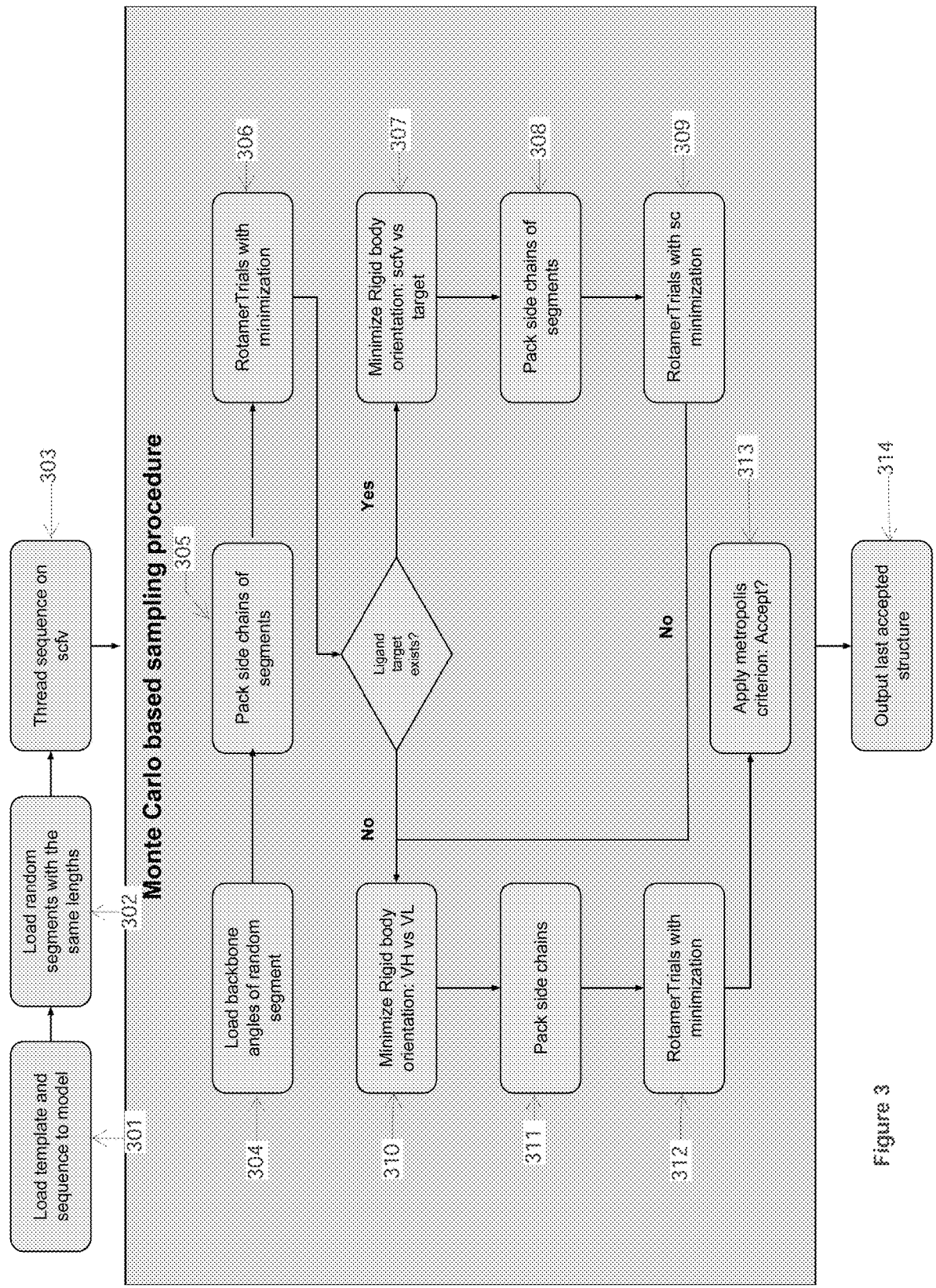
FIG. 3 illustrates a flow chart of a method for modeling of an antibody from sequence, according to one embodiment of the invention.
Figure 4:
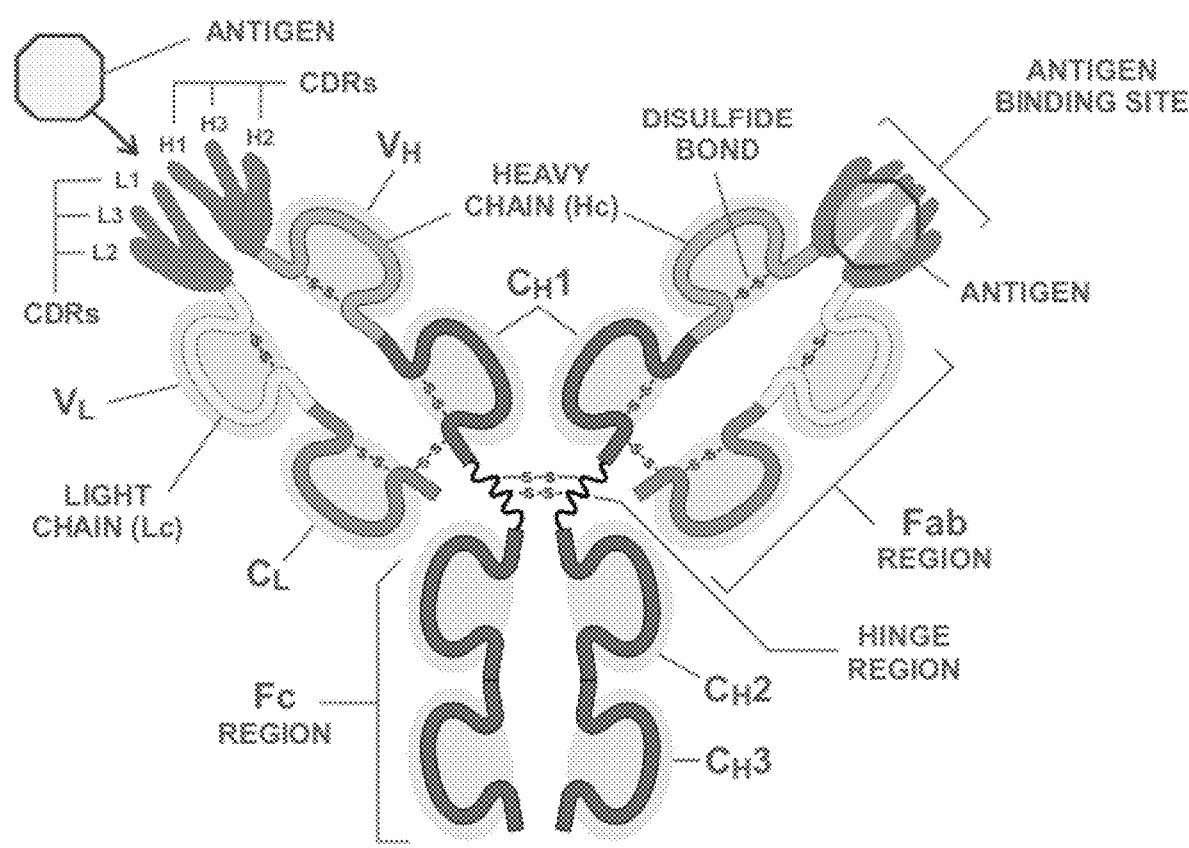
FIG. 4 shows a schematic drawing of an antibody molecule.

FIG. 3 schematically illustrates a flowchart of a method for modeling of an antibody from its sequence, according to one embodiment of the invention. In one embodiment, the structure of an antibody-antigen complex is modeled. In another embodiment, the structure of an unbound antibody is modeled. As shown in item 301, the structural template and the sequence of the antibody under examination are uploaded into an analysis system. In one embodiment, the template is placed in a desired position and orientation relative to a target epitope, as described in item 201 (see FIG. 2). As shown in item 302, backbone dihedral angle of a random segment are loaded for each segment of the structural template from the segment database. In one embodiment, the segment is selected to have the same length as the segment of the structural template. In another embodiment, the structural template segments comprise VH, corresponding to VH residues 1-99, H3 loop, VL, corresponding to VL residues 1-87, and an L3 loop. As shown in item 303, the sequence of the antibody under examination is threaded onto a ScFv structural template. After placing the template, a Monte-Carlo procedure with metropolis acceptance criteria is carried out for every entry in the segment database (item 114 in FIG. 1) for a preset number of iterations (K), as shown in items 304-314, in order to optimize the structural model. As shown in item 304, the backbone dihedral angles of a segment from the segment database are input into simulation. As shown in item 305, the side chains are packed in the selected segment. As shown in item 306, Rotamer-Trials Minimization is performed. In one embodiment, the RotamerTrials are performed until the score of the complex shows an insignificant change between iterations. In another embodiment, the RotamerTrials are performed for a predetermined number of iterations. In one embodiment, the rotamer trials are performed for at least 5 iterations, at least 6 iterations, at least 7 iterations, at least 8 iterations, at least 9 iterations, at least 10 iterations, or for more than 10 iterations. As shown in item 307, rigid body minimization of ScFv versus the target is performed. As shown in item 308, the side chains are packed in the selected segment in a way similar to item 305. As shown in item 309, cyclical Rotamer-Trials Minimization are performed in a way similar to item 306. As shown in item 310, rigid body minimization of VH versus VL is performed. As shown in item 311, the side chains are packed in the selected segment in a way similar to item 305. As shown in item 312, cyclical Rotamer-Trials Minimization is performed in a way similar to item 306. As shown in item 313, structural models that pass predefined metropolis acceptance criteria are accepted for output (item 314). Also contemplated are additional rounds of optimization prior to output (between items 313 and 314 in FIG. 3) generally comprising steps of side chain packing, rotamer trials and an additional step, wherein the additional step is optimizing the backbone of antibody, optimizing the light and heavy chain orientation, or optimizing the antibody as monomer. As a result, a structural model of an antibody-antigen complex is generated. In some embodiments, the docking steps and items 307-309 are omitted when the structure of an unbound antibody is modeled, to generate an unbound antibody structural model.

The following examples are presented in order to more fully illustrate the preferred embodiments of the invention. They should in no way be construed, however, as limiting the broad scope of the invention.

EXAMPLES

Embodiments of this invention utilize computational processing power to compute optimal antibody molecules, as well as structural models of antibody-antigen interfaces and of unbound complementarity determining regions. Provided herein are methods and systems to determine optimal antibody molecules that comprise the library Example 1

In this Example, computational processing power is used to compute antibody structural models that bind an epitope of a selected target polypeptide. Given a computer system and macro molecular modeling software that is able to approximate the free energy of a protein molecule (a.k.a free energy score, and/or score may be used interchangeably) the process is detailed below and is divided into 3 stages:
1. Creating a Point Specific Scoring Matrix (PSSM) for antibody segments
2. Creating a segment database
3. Designing an antibody for a target The first step in this process is to build a database of antibody CDR backbone segments, in particular, computing backbone phi, psi, and omega angles from known antibody crystal structures. Each of the two first stages generates the input for the next stage. In the next step, these parameters are then mixed and matched using macromolecular modeling software to either compute an optimal sequence for the purpose of designing a de-novo new model of antibody binder towards a particular target, or predict an unknown antibody structure given a sequence.

Stage 1: Creating a Point Specific Scoring Matrix (PSSM) for Antibody Segments:
1. Partition each of the segments according to their length;
2. For each different segments with equal lengths:
   a. Cluster the segments according to RMSD;
   b. For each cluster, generate a PSSM (using psi-blast or any equivalent tool).

Stage 2: Creating a Segment Database (See FIG. 1):
1. Choose an antibody structure to serve as a template;
2. Collect all non-redundant (99% sequence identity cut-off) high resolution (<3.0 Å) antibody models;
3. Extract the ScFv portion from the models;
4. Cut each ScFv into 4 segments (chothia numbering):
   a. VH Residues 1-91;
   b. 92-END;
   c. VL residues 1-87;
   d. VL residues 88-END.
5. For each segment:
   a. While N<10:
      i. Copy the dihedral angles of the segment to the respective segment of the template
      ii. Load the PSSM that corresponds to that segment
      iii. Insert a chain-break to a random position in the segment, that is not part of a secondary structure (helix or β-sheet)
      iv. Use a macro-molecular modeling software suite (e.g. Rosetta) to run a loop closure algorithm (either CCD or Kinematic loop closure) for K iterations, in an attempt to close the loop.
      v. Restrain the energy function in a way that:
         1. penalizes large deviations from the original dihedral angles or the XYZ coordinates of the backbone atoms.
         2. Favors backbone perturbations that bring the C and N terminals of both sides of the cut to be within range of a peptide bond (i.e. 1.33 Å±1 std)
         3. Favor sequences with high likelihood (computed w.r.t the PSSM)
      vi. Between each perturbation of the backbone done by the loop closure algorithm, apply side-chain packing and minimization, as well as sequence optimization. (Inserting amino acids that result in optimal score)
      vii. Do not allow introducing amino acids that have likelihood lower than a predefined threshold at a particular position, according to the PSSM
      viii. If the loop is not closed after K iterations of CCD/Kinematic loop closure, return to step a.i, increment N by 1.
      ix. If after K iterations, the RMSD of the modeled segment is smaller than X (X should be pre-defined, usually between 0<X<1 angstrom) Add the segment to the DB. Otherwise, increment N by 1, return to step a.i
   6. If the segment failed to pass the conditions above after 10 iterations, discard it.
   7. If the segment passed the conditions above after 10 iterations or less, add it to database Stage 3 Design an Antibody Structural Model for a Target (See FIG. 2):
Use a macro-molecular modeling software (such as Rosetta) to perform the following steps:
1. Place the template in the desired position and orientation towards the target epitope. This can be done by either using docking software or superimposing the template on an existing antibody-antigen complex.
2. Run the following Monte-Carlo procedure with the metropolis acceptance criteria for K iterations:
   a. Load the backbone dihedral angles of a randomly selected segment from the database that was created in Stage 2
   b. Load the PSSM that match each of the selected segments
   c. Modify the default scoring function of the macro-molecular modeling software:
      i. Introduce a scoring term that favors sequences with high likelihood, with respect to the previously computed PSSM
   d. Using the PSSM, for each position select a set of amino acids that pass a predefined likelihood threshold.
   e. Run a Design procedure: For each position in the segment and in a sphere of a predefined distance from it (~10 Å), use the amino acids selected in the above step to optimize the sequence w.r.t the scoring function of the macro-molecular modeling software
   f. Pack the side chains in the selected segment and in a sphere of a predefined distance (~10 Å) around the segment
   g. Run Rotamer-Trials Minimization procedure: Repeat until the score of the complex converges (e.g. delta between two iterations <−2) or number of iterations ≥5:
      i. For each side chain in the segment and in a sphere of a predefined distance (e.g. 10 Å), Find the rotamer with the minimal energy
   h. Run a rigid body minimization procedure, allowing the ScFv to sample the 6 degrees of freedom w.r.t the target
   i. Pack the segment's side chains and the side chains that are located in a sphere of a predefined distance from it, and run Rotamer-Trials with minimization (identical to g)
   j. Run a design procedure (identical to e)
   k. Run a rigid body minimization procedure, allowing the VH/VL segments to sample the 6 degrees of freedom w.r.t each other.
   l. Run a design procedure (identical to e)
   m. Pack the segment's side chains and the side chains that are located in a sphere of a predefined distance from it, and run Rotamer-Trials with minimization (identical to g)
   n. Accept the new structural model, if it passes the metropolis acceptance criterion (with the given structural model score as a parameter)
3. Output the structural model that was last accepted by the Monte-Carlo method Example 2

In this Example, computational processing power is used to compute the structural model of an antibody-antigen interface for an antibody bound to an epitope of a selected target polypeptide, as well as to compute the structural model of unbound complementarity determining region (CDR) for an antibody. Given a computer system and macro molecular modeling software that is able to approximate the free energy of a protein molecule (a.k.a free energy score, and/or score may be used interchangeably) the process is detailed below and is divided into 3 stages:

1. Creating a Point Specific Scoring Matrix (PSSM) for antibody segments;
2. Creating a segment database;
3. Modeling an antibody from sequence.

The first two stages in this Example are similar to those outlined in Example 1.

Stage 3 Model an Antibody from Sequence

Figure 5:
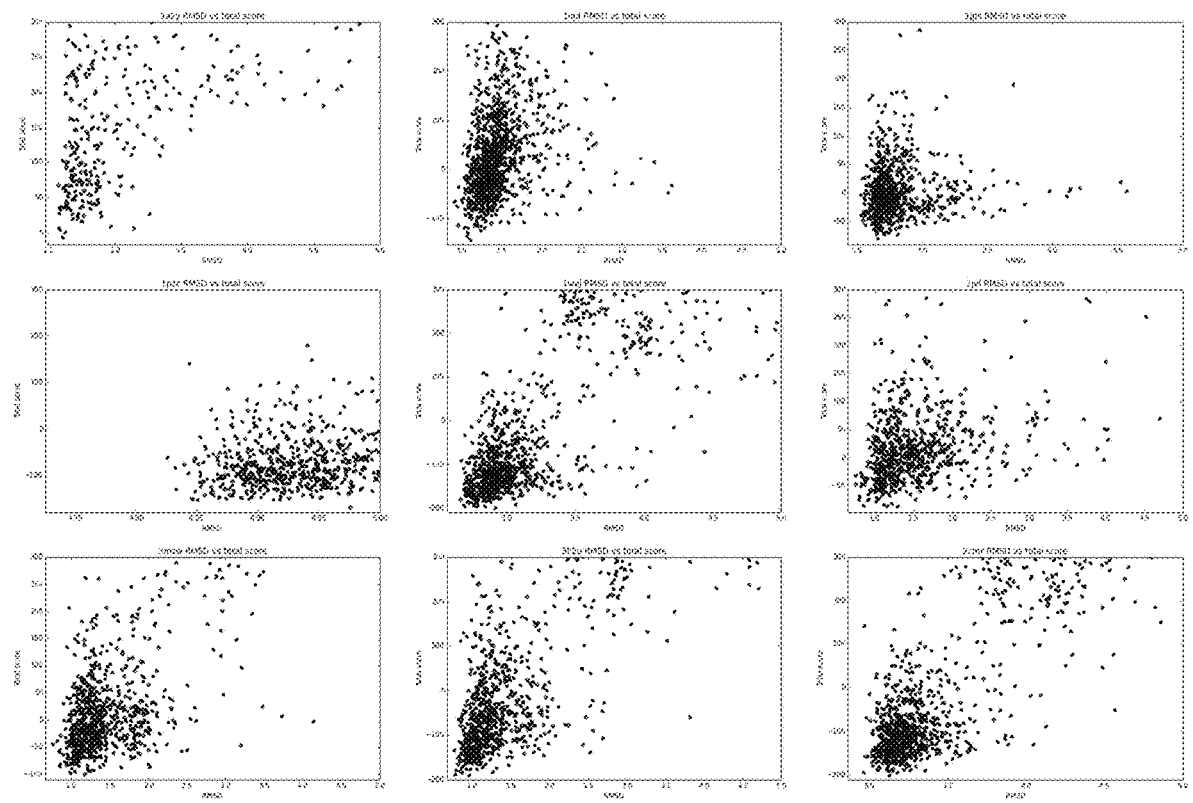
FIG. 5 shows score vs. RMSD plots calculated over all the atoms of the ScFv (antibody modeling). Each plot is an attempt to predict a different antibody (ScFv) structure. A point on each of the graphs represents a modeling trajectory. The X-axis is the distance (RMSD) of a modeling trajectory from the native structure. The Y-axis is the score the resulting output structural model received at the end of the trajectory.
Figure 6:
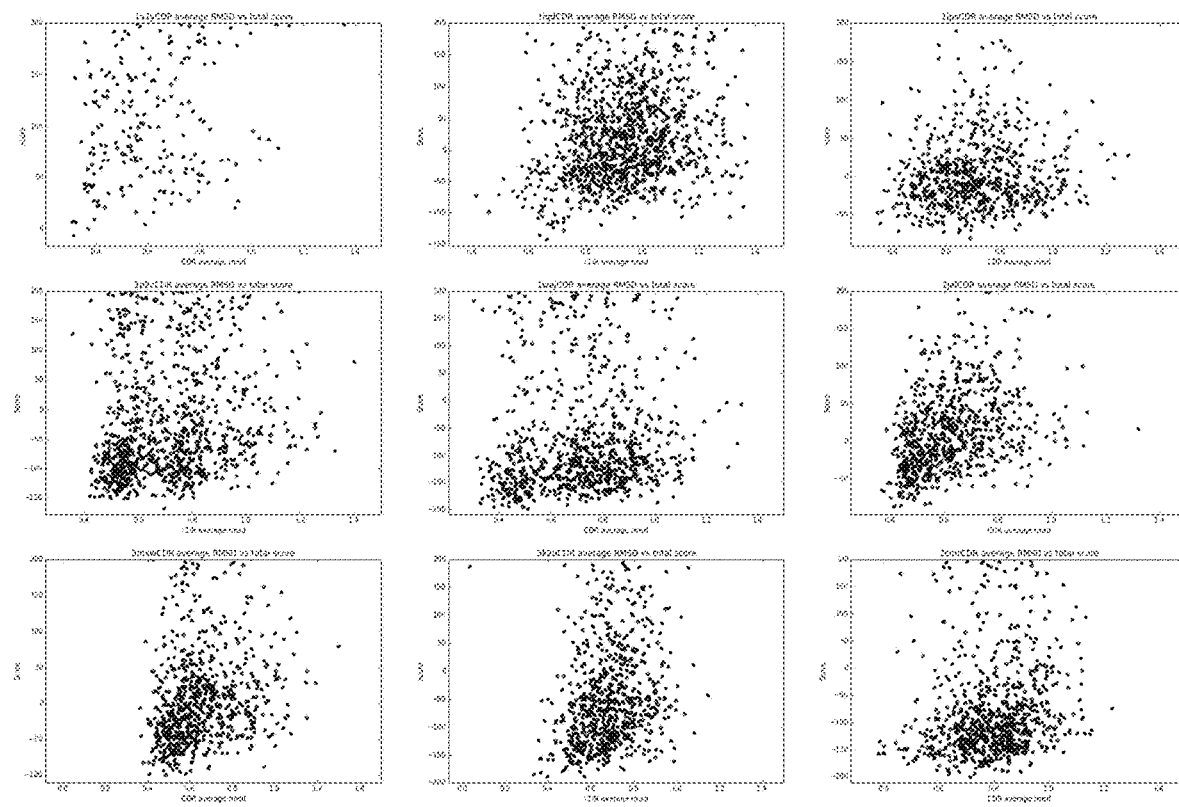
FIG. 6 shows total score vs. RMSD plots calculated over all the backbone atoms of the CDRs only (antibody modeling). Each plot is an attempt to predict a different antibody (ScFv) structure. A point on each of the graphs represents a modeling trajectory. The X-axis is the distance (RMSD) of a modeling trajectory from the native structure. The Y-axis is the score the resulting output structural model received at the end of the trajectory.

Use a macro-molecular modeling software (such as Rosetta) to perform the following steps:
1. Load the template PDB file and the antibody sequence
2. If the modeling is done in the presence of a target ligand, dock the template in the desired position on the target ligand using a docking software or superimposition
3. For each segment in the template (VH, H3, VL, L3) load the backbone dihedral angle of random segment with the same length from the segment database that was created in Stage 2
4. Thread the antibody sequence on the ScFv
5. Run the following Monte-Carlo procedure for K iterations:
   a. Load the backbone dihedral angles of a randomly selected segment from the database that was created in Stage 2
   b. Pack the side chains in the selected segment and in a sphere of a predefined distance (~10 Å) around the segment
   c. Run Rotamer-Trials Minimization procedure: Repeat until the score of the complex converges (e.g. delta between two iterations <−2) or number of iterations ≥5:
      i. For each side chain in the segment and in a sphere of a predefined distance (e.g. 10 Å), Find the rotamer with the minimal energy
   d. If a target exists in the simulation, run a rigid body minimization procedure, allowing the ScFv to sample the 6 degrees of freedom w.r.t the target
   e. Pack the segment's side chains and the side chains that are located in a sphere of a predefined distance from it, and run Rotmer-Trials with minimization (identical to g)
   f. Run a rigid body minimization procedure, allowing the VH/VL segments to sample the 6 degrees of freedom w.r.t each other.
   g. Pack the segment's side chains and the side chains that are located in a sphere of a predefined distance from it, and run Rotmer-Trials with minimization (identical to g)
   h. Accept the new structural model, if it passes the Monte-Carlo acceptance criteria (with the given structural model score as a parameter)
6. Output the structural model that was last accepted by the Monte-Carlo method FIGS. 5 and 6 are plots of ab-initio modeling runs made with according to above method. FIG. 5 shows score vs. RMSD plots calculated over all the atoms of the ScFv (antibody modeling). FIG. 6 shows total score vs. RMSD plots calculated over all the backbone atoms of the CDRs only (antibody modeling). A point on each of the graphs represents a modeling trajectory. The X-axis is the distance (RMSD) of a modeling trajectory from the native structure. The Y-axis is the score the resulting output structural model received at the end of the trajectory. Protein binding is often a process with a rugged energy landscape. Therefore, trajectories usually fall to local non-global minima. An ideal plot should have a concentration of models where y is minimal and x is close to zero.

Figure 7:
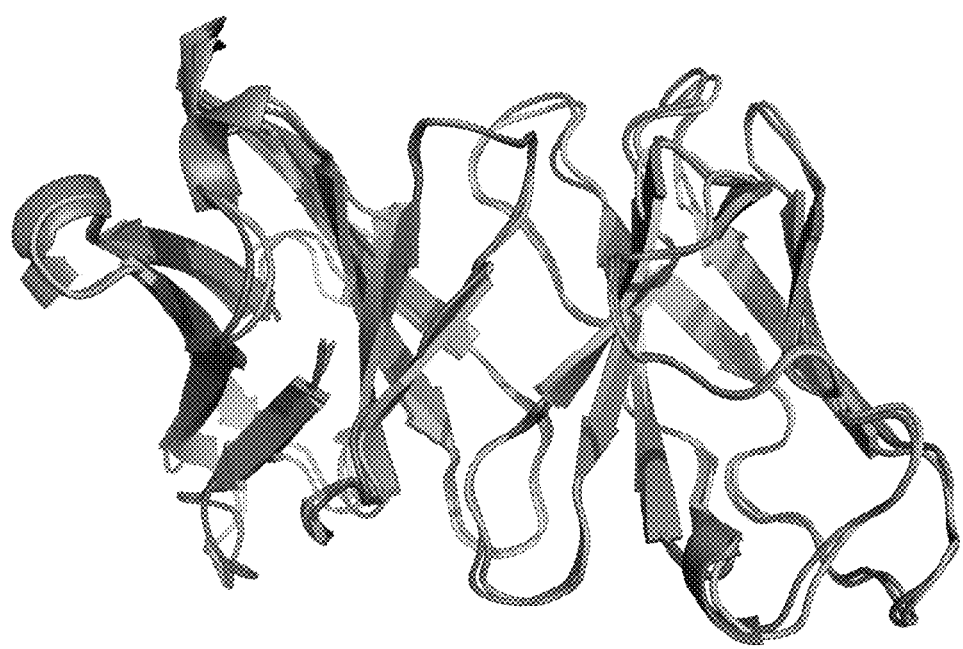
FIG. 7 shows a cartoon image of best scoring antibody (allosteric inhibitory antibody Fab40, targeted at HGFA (PDB id 3K2U)) model vs. native. Model in Magenta, native structure in Cyan. RMSD=0.6.
Figure 8:
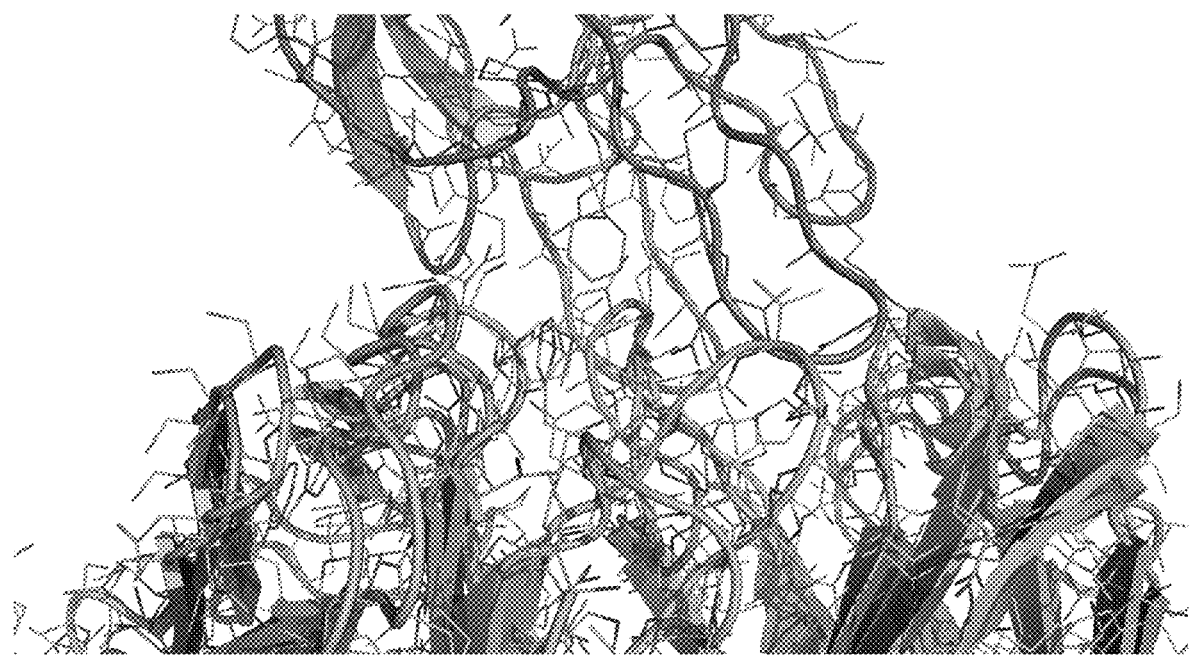
FIG. 8 shows a cartoon image of a designed mAb targeted at Human Factor VIII C2 Domain superimposed on crystal structure of human monoclonal BO2C11 Fab (PDB: 1IQD). In light green—the designed antibody, magenta—the ligand, cyan—BO2C11 (PDB: 1IQD).

FIG. 7 shows a cartoon image of best scoring antibody (allosteric inhibitory antibody Fab40, targeted at HGFA (PDB id 3K2U)) model vs. native (Model in Magenta, native structure in Cyan; RMSD=0.6). FIG. 8 shows a cartoon image of a mAb targeted at Human Factor VIII C2 Domain designed using the methods above, and that is superimposed on crystal structure of human monoclonal BO2C11 Fab (light green—the designed antibody, magenta—the ligand, cyan—BO2C11 (PDB: 1IQD)).

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A computer implemented method or a computer readable storage media comprising instructions to perform a method for generating a library of antibody models to an epitope, the method comprising:
   providing a sequence database of complementarity determining regions (CDRs) and a database of backbone dihedral angles for CDR segments compatible with a preselected structural template and based on known antibody 3-D structures comprising the steps of:
   selecting an antibody structure to serve as a template;
   obtaining a set of non-redundant high resolution antibody models;
   extracting the ScFv portion from each antibody model;
   cutting each ScFv into four segments, wherein the segments are:
   VH residues 1-99,
   an H3 loop,
   VL residues 1-87, and
   an L3 loop;
   generating a Point Specific Scoring Matrix (PSSM) for each segment; and
   generating database entries for each segment using a macromolecular algorithmic unit, wherein said macromolecular algorithmic unit cyclically optimizes or modifies the amino acid sequence based on the predetermined Point Specific Scoring Matrix (PSSM) and Root Mean Square Deviation (RSMD) of the modeled segment, wherein sequences having an RSMD below a predetermined threshold following a predetermined number of optimization/modification cycles are included in the database;
   docking said preselected structural template on said epitope;
   evaluating one or more sequences from said databases using a simulated annealing process; and
   identifying one or more segment sequences in order to generate a library, thereby generating a library of antibody models to the epitope.

2. The method of claim 1, wherein said annealing process is performed by a Monte Carlo simulation with metropolis acceptance criteria.

3. The method of claim 2, wherein said annealing process comprises optimizing the packing of side chains, VH-VL rigid body minimization, antibody-ligand rigid body minimization, antibody VH-VL sequence optimization, optimizing the backbone of antibody, optimizing rotamers, optimizing the light and heavy chain orientation, optimizing the antibody as monomer, or a combination thereof.

4. The method of claim 3, wherein multiple iterations of said Monte Carlo simulation are performed, wherein a structural model is accepted if it passes predetermined metropolis acceptance criteria after a predetermined number of iterations.

5. The method of claim 1, wherein each cycle of said cyclical optimization further comprises inserting a chain break at a random position that is not a part of secondary structure ($\alpha$-helix or ($\beta$-sheet).

6. The method of claim 1, wherein said cyclical optimization further comprises evaluation of each segment or a combination thereof, using a cyclical loop closure process repeated over a predetermined number of cycles.

7. The method of claim 6, wherein said cyclical loop closure process evaluates segments based on sequence optimization, side chain packing, side chain minimization and energy function.

8. The method of claim 1, wherein said epitope is a protein.

* * * * *